(12) United States Patent
Utas et al.

(10) Patent No.: US 8,267,919 B2
(45) Date of Patent: Sep. 18, 2012

(54) CATHETER ASSEMBLY WITH OSMOLALITY-INCREASING FLUID

(75) Inventors: Jan Utas, Kungsbacka (SE); Kristina Kull, Öjersjö (SE)

(73) Assignee: Astra Tech AB, Molndal (SE)

( * ) Notice: Subject to any disclaimer, the term of this patent is extended or adjusted under 35 U.S.C. 154(b) by 1385 days.

(21) Appl. No.: 10/584,073

(22) PCT Filed: Dec. 22, 2004

(86) PCT No.: PCT/SE2004/001979
§ 371 (c)(1),
(2), (4) Date: Sep. 20, 2006

(87) PCT Pub. No.: WO2005/061035
PCT Pub. Date: Jul. 7, 2005

(65) Prior Publication Data
US 2007/0149929 A1  Jun. 28, 2007

(30) Foreign Application Priority Data
Dec. 22, 2003  (SE) ........................................ 0303525

(51) Int. Cl.
*A61M 1/00* (2006.01)
(52) U.S. Cl. ........................................ 604/544; 604/317
(58) Field of Classification Search .................. 604/540, 604/544, 319, 322; 206/363, 364
See application file for complete search history.

(56) References Cited

U.S. PATENT DOCUMENTS
6,409,717 B1  6/2002  Israelsson et al.
2005/0137582 A1  6/2005  Kull-Osterlin et al.

FOREIGN PATENT DOCUMENTS
EP  0 217 771 A1  4/1987
EP  217771 A1 *  4/1987
(Continued)

OTHER PUBLICATIONS
Bongard, Frederic S. et al, "Current Critical Care Diagnosis & Treatment", 2002, p. 30.*

(Continued)

*Primary Examiner* — Melanie Hand
(74) *Attorney, Agent, or Firm* — Birch, Stewart, Kolasch & Birch, LLP (57) ABSTRACT

A catheter assembly is disclosed comprising: a hydrophilic catheter; a wetting fluid for wetting of the catheter; and a receptacle enclosing at least the insertable part of the catheter and the wetting fluid. Further, the wetting fluid is a solution incorporating at least one osmolality-increasing compound, and the total concentration of the osmolality-increasing compound(s) is very high, preferably exceeding 600 mOsm/dm$^3$. The wetting fluid could either be arranged in contact with the hydrophilic surface layer of the catheter in the receptacle, for preservation of the hydrophilic surface layer in a wetted state during accommodation in said receptacle and provision of a ready-to-use catheter assembly, or be arranged to keep the wetting fluid separated from the hydrophilic surface layer of the catheter during storage, but to be brought into contact with said hydrophilic surface layer upon activation before an intended use of the catheter. A similar method and wetting fluid is disclosed as well. The provision of the osmolality-increasing compound in the wetting fluid provides several advantages per se, such as a improved properties of the hydrophilic coating, a more predictable and controllable wetting process, a more expedient and cost efficient production, etc. Further, the use of this very high concentration of osmolality-increasing compound in the wetting fluid has proven remarkably efficient.

28 Claims, 5 Drawing Sheets

FOREIGN PATENT DOCUMENTS

| | | |
|---|---|---|
| EP | 0 586 324 A1 | 3/1994 |
| EP | 0 591 091 A1 | 4/1994 |
| EP | 0 991 702 B1 | 8/2001 |
| WO | WO-94/16747 A1 | 8/1994 |
| WO | WO-97/26937 A1 | 7/1997 |
| WO | WO 9726937 A1 * | 7/1997 |
| WO | WO-98/11932 A1 | 3/1998 |
| WO | WO-98/19729 A1 | 5/1998 |
| WO | WO-98/58989 A1 | 12/1998 |
| WO | WO-00/47494 A1 | 8/2000 |
| WO | WO 0047494 A1 * | 8/2000 |
| WO | WO-01/43807 A1 | 6/2001 |

OTHER PUBLICATIONS

L. Waller et al., Spinal Cord, vol. 35, No. 3, 1997, pp. 229-233.
J. Lundgren et al., Spinal Cord, vol. 38, 2000, pp. 45-50.
M. Sovak, MD et al., Invist Radiol. Sep. 23, 1988, pp. 84-87.
Bongard et al., "Current Critical Care Diagnosis & Treatment", 2002, p. 30—Hypersonic Saline and Furosemide.

* cited by examiner

CATHETER ASSEMBLY WITH OSMOLALITY-INCREASING FLUID

FIELD OF THE INVENTION

The present invention relates to a catheter assembly of the type comprising a receptacle, a hydrophilic catheter and a wetting fluid. Further, the invention relates to a method for producing such a catheter assembly, as well as a wetting fluid and the use thereof for wetting of a hydrophilic surface layer The invention also relates to a catheter as such.

BACKGROUND OF THE INVENTION

Catheters find their use in many different medical applications, such as urinary catheters for bladder drainage. Each catheter is normally pre-packed in a receptacle by the manufacturer, in order to maintain the catheter in a clean and preferably sterile condition.

A urinary catheter in general need to have a lubricant applied to the outer surface thereof to facilitate insertion into the urethra. Especially, for lubrication purposes, a hydrophilic urinary catheter may have a hydrophilic outer surface coating or layer which should be wetted by a fluid such as water for a certain time period prior to insertion of the catheter into the urethra of a patient. In order to facilitate the use and to improve cleanliness of the catheter, the assemblies have in recent years developed to comprise a rupturable wetting fluid pouch or container as well. Such assemblies are disclosed in e.g. WO 97/26937, WO 01/43807 and WO 98/11932.

Further, there has been a trend towards so-called "ready-to-use" catheters, where the catheter is arranged in the receptacle together with a wetting fluid in such a way that the catheter is maintained in a wetted, activated condition by said fluid. Such ready-to-use catheter assemblies are disclosed in e.g. WO 00/47494 and WO 98/19729.

A well-recognized problem with hydrophilic coatings or layers has been that the hydrophilic polymer surface may lose water and dry out when it comes in contact with e.g. a mucous membrane, such as when the catheter is inserted into the urethra. This occurs because of a difference between the osmotic potential of the hydrophilic surface and the osmotic potential of the mucous membrane. The mucous membrane has a higher osmotic potential, i.e. a higher salt concentration, than the hydrophilic surface. This difference in osmotic potential causes the water to go from the hydrophilic surface layer to the mucous membrane so that the difference in the salt concentration will be counter-balanced. Naturally, this affects the low-friction properties of the hydrophilic outer surface coating, and may lead to pain and injuries of the patient.

For this reason, the present applicant has previously developed an improved hydrophilic coating, in which an osmolality-increasing compound was applied to a non-reactive hydrophilic polymer surface, thereby producing a more stable hydrophilic surface, as is disclosed in EP 217 771. Hereby, the theretofore prevailing problem of the hydrophilic coating drying out when inserted into the urethra, thus rendering the article insufficiently hydrophilic, was alleviated.

Similar hydrophilic coatings incorporating an osmolality-increasing compound are discussed in WO 94/16747 disclosing a process in which the osmolality-increasing compound is added during the process of applying the hydrophilic coating to the base material, EP 586 324 and EP 591 091 disclosing a hydrophilic coating comprising a non-dissolved, solid osmolality-increasing compound e.g. in the form of a powder or grain, and EP 991 702 disclosing a cross-linked hydrophilic coating comprising a water soluble osmolality-increasing compound.

However, these known methods and coatings are affected by some problems. For example, the production processes, involving different manners of incorporating the osmolality-increasing compounds in the coatings, are rather tedious cumbersome and costly. Further, the properties of the resulting, wetted hydrophilic surface coating to be inserted into the patient are, at least to a certain extent, affected by parameters of the wetting process, such as the quantity of wetting fluid used for the wetting, the constituents of the chosen wetting fluid, and the time period during which the wetting is carried through. Since several such parameters may be unknown beforehand, and may vary to a significant degree, the properties of the resulting, activated coating become unpredictable as well.

WO 00/47494 discloses a ready-to-use catheter product in which a wetting fluid is arranged in a receptacle in direct contact with a hydrophilic surface of a catheter, thereby continuously maintaining the hydrophilic surface in an activated state. This document discloses the use a saline solution as the wetting fluid. However, no information is given about any specific concentration of salt in the wetting fluid.

SUMMARY OF THE INVENTION

It is a general object of the present invention to alleviate the above-discussed problems.

This object is achieved with a catheter assembly, a production method, a wetting fluid, and a method of use according to the appended claims.

According to a first aspect, there is provided a catheter assembly comprising: a wetting fluid; a catheter having on its surface, on at least an insertable part thereof, a hydrophilic surface layer providing low-friction surface character of the catheter by treatment with said wetting fluid; and a receptacle enclosing at least the insertable part of the catheter. The wetting fluid comprises at least one dissolved osmolality-increasing compound, wherein the total concentration of the dissolved osmolality-increasing compound(s) exceeds 600 mOsm/dm$^3$.

The unit milliosmole (mOsm), i.e. one-thousandth of an osmole, represents the amount of substance that dissolves in a solvent to form one mole of osmotically active units (atoms, ions, etc), e.g., 1 mole of glucose, which is not ionizable, forms 1 osmole of solute, but 1 mole of sodium chloride forms 2 osmoles of solute.

The wetting fluid may be arranged in wetting contact with the hydrophilic surface layer or coating of the catheter in the receptacle, for preservation of the hydrophilic surface layer in a wetted state during accommodation in said receptacle, whereby a ready-to-use catheter assembly is provided. The assembly may also be such that the wetting fluid is initially kept separated from the hydrophilic surface layer of the catheter during storage of the assembly, and brought into contact with the hydrophilic surface layer upon activation before an intended use of the catheter.

This very high concentration of osmolality-increasing compound, exceeding 600 mOsm/dm$^3$, in the wetting fluid has, proven remarkably efficient. Specifically, the high concentration according to the invention is in line with the normal saline concentration in urine (which is about 900 mOsm/dm$^3$) and is much higher than the concentration in a physiological saline solution (about 290 mOsm/dm$^3$). It has surprisingly been found by the present inventors that when a such a high concentration is used for the wetting fluid, the properties of the resulting wetted hydrophilic layer is dramatically improved in respect of e.g. stability during wetting, and thereby stability during use, friction, and in particular a lowered extraction force, and water retention.

A further surprising advantage achieved by the present invention is a significantly lowered risk for crystalline growth on the catheter surface, and a significant lowered sensitivity for ambient moisture. In catheters where a corresponding concentration of osmolality increasing compound is arranged directly on the catheter surface, the catheter becomes sensitive to moist, and if moist penetrates the enclosing package there is a risk that crystals will grow on the surface, which may cause pain for the patient. This risk obviously becomes greater when the concentration of osmolality increasing compound is increased. Here, the osmolality increasing compound is dissolved in the wetting fluid, where no risk for crystalline growth exist, and thereby the overall risk for crystalline growth on the catheter surface is significantly reduced, and the moisture sensitivity becomes essentially unrelated to the concentration of the osmolality increasing compound.

It has been found by the present inventors that such a high concentration leads to an extremely stable and reliable wetted hydrophilic surface, and no negative side-effects has been noted.

In a preferred embodiment, the total concentration of the osmolality-increasing compound(s) in the wetting fluid is exceeding 700 mOsm/dm$^3$, preferably exceeding 800 mOsm/dm$^3$.

In an especially preferred embodiment the total concentration of the osmolality-increasing compound(s) in the wetting fluid solution is in the range of 850 mOsm/dm$^3$ to 950 mOsm/dm$^3$, preferably about 900 mOsm/dm$^3$.

It is preferred that the total concentration of the osmolality-increasing compound(s) in the wetting fluid is less than 1500 mOsm/dm$^3$.

The osmolality-increasing compound(s) is/are preferably selected from the group consisting of urea, amino acids, mono and disaccharides, sugar alcohols, and non-toxic organic and inorganic salts or acids, polypeptides and mixtures thereof.

The present invention also encompasses embodiments in which one or more osmolality-increasing compound(s) are provided not only in the wetting fluid with the high concentration according to the inventive concept, but also in a hydrophilic layer on the catheter.

The present invention is particularly useful for urinary catheters, and especially for single-use urinary catheters intended for intermittent use.

The provision of one or more dissolved osmolatity-increasing compounds in the wetting fluid provides several advantages. First of all, essentially the same advantages as achieved by adding osmolality-increasing compounds to the layer, also applies to the hydrophilic layer when wetted with a wetting fluid incorporating an osmolality-increasing compound. Accordingly, the hydrophilic coating in its state of use becomes more stable than if no osmolality-increasing compound was used, thereby rendering the hydrophilic coating less likely to dry out when inserted into the urethra and more capable of retaining its low friction characteristics.

Further, the addition of an osmolality-increasing compound to the wetting fluid is a relatively simple procedure, whereby the production becomes much more expedient and cost effective than in the previously known methods.

Still further, the properties of the hydrophilic layer as wetted with the wetting fluid incorporating one or more osmolality-increasing compounds are, in several aspects, superior and more reliable compared to the properties of a coating into which the osmolality-increasing compounds has been added. This is inter alia due to the fact that the steps leading to the final product, viz. the wetted, low-friction surface, are more predictable and determinable in case of the present invention. For example, the present invention gives the manufacturer full control of parameters such as the quantity of wetting fluid used for the wetting and the constituents of the chosen wetting fluid. In many previously known methods, it is often difficult to predict which wetting fluid the user will make use of, e.g. sterile water or ordinary local tap water, and thereby the constituents of said fluid. It is also difficult to predict what amount of fluid the user will use.

The wetting fluid preferably also includes a polymer. The polymer is preferably a hydrophilic polymer, and most preferably the same type of hydrophilic polymer as in the hydrophilic coating of the catheter. The amount of polymer in the wetting fluid could be in the range 0-20% of weight, and most preferably in the range 5-15%, and typically about 10%. The addition of such a polymer into the wetting fluid provides a significant improvement of the slipperiness of the hydrophilic surface of the catheter when wetted by the wetting fluid.

In addition, the properties of the hydrophilic coating as wetted with a wetting fluid comprising at least one dissolved osmolality-increasing compound are less dependent on the length of the time period during which the wetting occurs, compared to the properties of coatings into which the osmolality-increasing compounds are added. This is probably due to more homogenous conditions between the coating and the wetting fluid, in which a relatively stable equilibrium in respect of the osmolality-increasing constituents is reached as soon as the hydrophilic coating becomes impregnated with the wetting fluid. Hereby, the final product, viz. the wetted, low-friction surface, becomes more predictable and determinable when the present invention is used, since the sensitivity to human errors and the like is significantly reduced.

According to a second aspect, there is provided a wetting fluid for activation of a hydrophilic surface layer in order to produce a low-friction surface character of said hydrophilic surface layer by treatment by said wetting fluid. The wetting fluid comprises at least one dissolved osmolality-increasing compound, wherein the total concentration of the osmolality-increasing compound(s) exceeds 600 mOsm/dm$^3$. The wetting fluid may be used as an integrated part in a catheter assembly, i.e. forming part of the assembly during storage, as discussed in the foregoing. However, it may also be arranged separately, for use together with e.g. catheters packed without wetting fluid being attached.

Similar advantages are provided by this second aspect as already discussed in view of the first aspect. Also, the above-mentioned embodiments regarding e.g. concentration levels and compounds apply to this second aspect also. Specifically, the provision of at least one dissolved osmolality-increasing compound in the wetting fluid provides several advantages per se, such as improved properties of the hydrophilic layer, a more predictable and controllable wetting process, a more expedient and cost efficient production, etc. Further, the use of this very high concentration of osmolality-increasing compound(s) in the wetting fluid has, as is already discussed in the foregoing, proven remarkably efficient.

According to a third aspect, there is provided a method for producing a catheter assembly, said method comprising: providing a receptacle; providing a hydrophilic catheter; providing a wetting fluid; arranging at least an insertable part of the catheter in the receptacle and arranging said wetting fluid as a part of said catheter assembly, said wetting fluid comprising at least one osmolality-increasing compound, the total concentration of the osmolality-increasing compound(s) exceeding 600 mOsm/dm$^3$.

According to a fourth aspect of the invention, a catheter is provided, having on its surface, on at least an insertable part thereof, a hydrophilic surface layer for producing a low-friction surface character of the catheter by treatment with a wetting fluid, wherein the hydrophilic coating when wetted in preparation for an intended use incorporates at least one osmolality-increasing compound, and the total concentration of the osmolality-increasing compound(s) exceeds 600 mOsm/dm$^3$.

Similar advantages are provided by this aspect of the invention as already discussed in view of the previous aspects of the invention. Specifically, the use of this very high concentration of osmolality-increasing compound in the wetted hydrophilic surface layer has, as is already discussed in the foregoing, proven remarkably efficient.

The osmolality increasing compound(s) may be dissolved in the wetting fluid, and thereby incorporated into the hydrophilic surface during the wetting process, as is already discussed in relation to the other aspects in the foregoing. Alternatively, osmolality increasing compound(s) may be incorporated into the hydrophilic coating before the wetting, but of a concentration high enough to provide a dissolved concentration of the osmolality-increasing compound(s) when wetted in preparation for an intended use exceeding 600 mOsm/dm$^3$. For incorporation of the osmolality-increasing compound(s) into the coating, any one of the per se known methods discussed in the background section may be used, such as e.g. the method disclosed in EP 217 771. Further, a combination of said alternative ways of providing the osmolality-increasing compound(s) are also feasible, whereby the osmolality-increasing compound(s) prior to the wetting process is both incorporated into the wetting fluid and into the hydrophilic coating of the catheter, wherein the concentrations in the wetting fluid and in the hydrophilic coating, respectively, are high enough to provide a total dissolved concentration of the osmolality-increasing compound(s) in the hydrophilic coating when wetted in preparation for an intended use exceeding 600 mOsm/dm$^3$.

It is also possible to arrange all, or at least part of the osmolality-increasing compound(s) on the catheter or on other parts of the catheter assembly subsequently exposed to the wetting fluid, whereby the osmolality-increasing compound(s) will dissolve in the wetting fluid when brought in contact with each other.

A fifth aspect of the invention relates to a use of a wetting fluid solution for activation of a catheter having on its surface, on at least an insertable part thereof, a hydrophilic surface layer providing low-friction surface character of the catheter by treatment with said wetting fluid, wherein the wetting fluid comprises at least one dissolved osmolality-increasing compound, and wherein the total concentration of the dissolved osmolality-increasing compound(s) exceeds 600 mOsm/dm$^3$.

Similar advantages are provided by this aspect of the invention as already discussed in view of the previous aspects of the invention. Specifically, the provision of at least one osmolality-increasing compound in the wetting fluid provides several advantages per se, such as improved properties of the hydrophilic coating, a more predictable and controllable wetting process, a more expedient and cost efficient production, etc. Further, the use of this very high concentration of osmolality-increasing compound in the wetting fluid has, as is already discussed in the foregoing, proven remarkably efficient.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, the dimensions of the fluid compartments, etc.

The Catheter

Hydrophilic catheters may be used for many different purposes, and for insertion into various types of body-cavities. However, the following discussion is in particular concerned with the preferred field of use, urinary catheters, even though the invention is not limited to this particular type of catheters.

Figure 1:
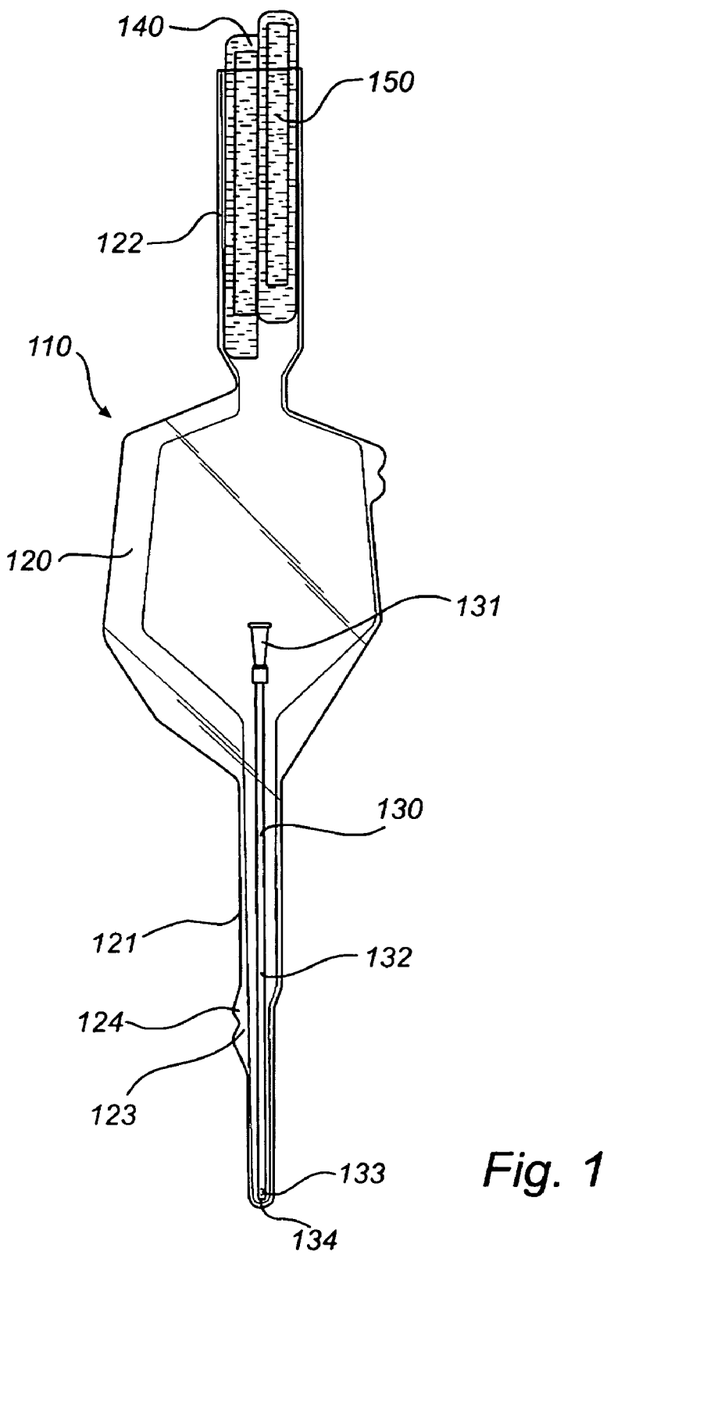
FIG. 1 illustrates a first embodiment of a catheter assembly according to the invention, presenting a separately enclosed wetting fluid, said embodiment in structure resembling a catheter assembly disclosed in WO 97/26937.

A catheter 130 as illustrated in the drawings, e.g. in FIG. 1, comprises a flared rearward portion 131 and an elongate shaft or tube 132 projecting forwardly from the rearward portion 131. An open-ended internal lumen (not shown) extends from the rear end of the rearward portion 131 to a drainage aperture 133 in a rounded tip 134 of the elongate tube 132. The rearward portion 131 may function as a connector of the catheter 130, being connectable to other devices, such as a urine collection bag, a drainage tube or the like.

At least a part of the elongate tube 132 forms an insertable length to be inserted through a body opening of the user, such as the urethra in case of a urinary catheter. By insertable length is normally, in the context of a hydrophilic catheter, meant that length of the elongate tube 132 which is coated with a hydrophilic material, for example PVP, and which is insertable into the urethra of the patient. Typically, this will be 80-140 mm for a female patient and 200-350 mm for a male patient.

According to the invention, and applicable for the embodiments disclosed herein, the wetting fluid may be used for the wetting of many different types of well-known hydrophilic surfaces. For example, the catheter may be provided with a hydrophilic coating wherein the hydrophilic polymer coating comprises material selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

The coating may also comprise an osmolality-increasing compound, as is e.g. taught in EP 0 217 771, even though this may, at least for some embodiments, be superfluous when using the wetting fluid as discussed in the following. However, in some embodiments, it may be useful to incorporate the osmolality-increasing compound(s) into both the wetting fluid and into the hydrophilic coating of the catheter, wherein the concentrations in the wetting fluid and in the hydrophilic coating, respectively, are high enough to provide a total dissolved concentration of the osmolality-increasing compound(s) in the hydrophilic coating when wetted in preparation for an intended use. Still further, it is also possible to incorporate the osmolality increasing compound(s) solely in the hydrophilic coating before the wetting, and in a concentration high enough to provide the intended dissolved concentration of the osmolality-increasing compound(s) when wetted in preparation for an intended use. For incorporation of the osmolality-increasing compound(s) into the coating, any one of the per se known methods discussed in the background section may be used, such as e.g. the method disclosed in EP 217 771.

The substrates may be made from any polymer material, which are well-known in the technical field and to which the said hydrophilic polymers adhere, such as polyurethanes, latex rubbers, other rubbers, polyvinylchloride, other vinyl polymers, polyesters and polyacrylates.

The Wetting Fluid

According to the invention, and in the embodiments disclosed herein, the wetting fluid serves the dual purposes of (i) wetting the hydrophilic surface coating, whereby a low-friction character of the surface is produced, and (ii) providing a dissolved osmolality-increasing compound to the wetted hydrophilic surface, thereby making the hydrophilic coating more stable and less likely to loose water and dry out during use. To this end, the wetting fluid comprises at least one dissolved osmolality-increasing compound.

Several different osmolality-increasing compounds are feasible for incorporation into the wetting fluid. Preferably, the osmolality-increasing compound(s) is selected from the group consisting of urea, amino acids, mono and disaccharides, sugar alcohols, and non-toxic organic and inorganic salts or acids, polypeptides and mixtures thereof. Most preferably, the osmolality-increasing compound(s) is selected from the group consisting of glucose, sorbitol, sodium chloride, sodium citrate, sodium benzoate, calcium chloride, potassium chloride, potassium iodide and potassium nitrate.

The wetting fluid is preferably a water-based liquid, i.e. using water as a solvent.

The concentration of osmolality-increasing compound(s) is relatively high in the solution, and e.g. exceeding the concentration in physiological saline, i.e. about 300 mOsm/dm$^3$. The total concentration of the osmolality-increasing compound(s) in the wetting fluid solution and/or in the hydrophilic coating when wetted in preparation for an intended use exceeds 600 mOsm/dm$^3$. Further, the total concentration of the osmolality-increasing compound(s) preferably exceeds 700 mOsm/dm$^3$ and most preferably exceeds 800 mOsm/dm$^3$. It is also preferred that the total concentration of the osmolality-increasing compound(s) is in the range 600-1500 mOsm/dm$^3$, and preferably in the range 850 to 950 mOsm/dm$^3$, and as a guiding value about 900 mOsm/dm$^3$.

Still further, the wetting fluid preferably also comprises a dissolved hydrophilic polymer, and preferably the same hydrophilic polymer as in the hydrophilic coating of the catheter for which the wetting fluid is intended. The amount of hydrophilic polymer in the wetting fluid is preferably in the range 0-20% of weight, and most preferably in the range 5-15%, and typically about 10%.

The Catheter Assembly

With reference to FIG. 1, a first embodiment of a catheter assembly will now be described, the structure of which generally resemblings embodiments previously disclosed in WO 97/26937, hereby incorporated by reference.

The catheter assembly 110 comprises a wetting receptacle or bag 120, preferably of a transparent flexible plastics material. The receptacle 120 has an elongate pocket 121 at its forward end. At its rearward end 122 the receptacle presents an opening. The wetting receptacle 120 is adapted for accommodation of at least the insertable length of the catheter tube 132 in the elongate pocket 121.

The catheter assembly 110 further comprises a hydrophilic urinary catheter 130, as is discussed in more detail in the foregoing.

The catheter assembly 110 comprises a wetting fluid 150 forming part of the assembly 110, i.e. the wetting fluid is not provided completely separate from the assembly. More specifically, in the embodiment in FIG. 1, the catheter assembly 110 further comprises a wetting fluid container 140, in which the wetting fluid 150 is kept separated from the hydrophilic surface of the catheter 130 during storage.

The wetting fluid container 140 is openable, in order to enable activation of the catheter assembly. Thus, the activation is performed by opening the container and releasing the wetting fluid into the wetting receptacle 120 so that it comes into contact with the hydrophilic coating of the catheter 130. The wetting fluid container 140 may be openable by means of pressing, tearing, piercing, twisting, etc, which is per se well-known in the art. The wetting fluid 150 is discussed in more detail in the foregoing.

The wetting receptacle 120 preferably forms a sealed compartment around the catheter 3 and at least part of the wetting fluid container 140.

The wetting receptacle 120 preferably comprises opening means for facilitating opening of the receptacle in order to expose the catheter 130 for use. The opening means may comprise a tear line 123 connected to a gripping handle 124, such as a pulling tab. Hereby, the user may pull the gripping handle 124 and, thereby, tearing open the side wall of the wetting receptacle 120. Additionally, or alternatively, a gripping handle may be arranged in the opposite end of the tear line 123. However, alternative opening means are also feasible, such as tear-lines arranged in different fashions and locations, peel-off joints, etc.

In a method of wetting the catheter 130 according to the embodiment in FIG. 1, the user first activates the catheter 130 by opening the wetting fluid container 140 within the bounds of the wetting receptacle 120, thereby releasing the wetting fluid from the container 140 into the wetting receptacle 130. After a sufficient wetting period, the wetting receptacle 120 is opened, in order to expose the catheter 130 for insertion into a patient.

In the embodiment in FIG. 1, the wetting receptacle 120 also serves as a urine collection bag. Thus, being opened, the receptacle 120 maintains connected to the catheter 120 for receiving the drained urine from the bladder.

Figure 2:
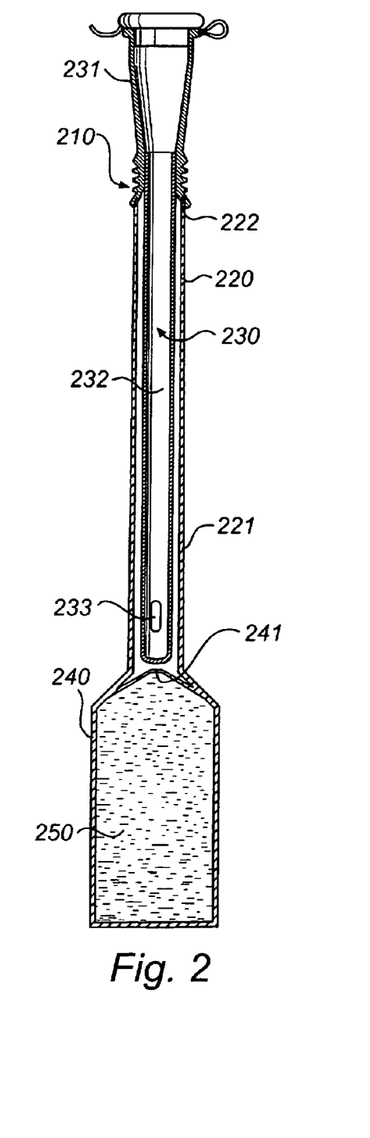
FIG. 2 is a partly broken side view of a second embodiment of a catheter assembly according to the invention, also presenting a separately enclosed wetting fluid, said embodiment in structure resembling a catheter assembly disclosed in WO 01/43807.

With reference to FIG. 2, a second embodiment of a catheter assembly will now be described, the structure of which resembling catheter assemblies disclosed in WO 01/43807, hereby incorporated by reference.

In this embodiment, the wetting receptacle 220 is adapted for accommodation of only the catheter tube 232 in the elongate pocket 221, whereas the opening end 222 of the wetting receptacle 220 is sealingly connected to and closed by the connector or rearward end 231 of the catheter 230. Hereby, the receptacle 220 encloses the insertable length of the catheter 230, but leaves a part of the catheter 230 outside the receptacle 220.

In the embodiment in FIG. 2, the wetting fluid container 240 enclosing the wetting fluid 250 is formed as a separate compartment of the wetting receptacle 220. A rupturable separation wall 241 is arranged between this receptacle compartment 240 holding the wetting fluid 250 and the receptacle compartment holding the catheter 230, i.e. the elongate pocket 221. The separation wall 241 may be provided by arranging a peelable joint between the compartments.

In a method of activating the catheter 230, the user applies a compressing force to the wetting fluid container 240 in such a way that the rupturable separation wall 241 is opened and the wetting fluid 250 is introduced into the catheter-holding compartment 221 of the wetting receptacle 220. It may be noted that the sealingly connection at the opening end 222 with the connector 231 maintains the wetting fluid 250 in the catheter-holding compartment 221. After release of the wetting fluid into the catheter compartment 221 and when the catheter has been activated, the receptacle 220 may be opened in order to expose the catheter 230 for use. The wetting receptacle 220 may either be ripped off from the wetted catheter 230 before use of the catheter and then disposed of, or be maintained connected to the catheter 230 during use.

Figure 3:
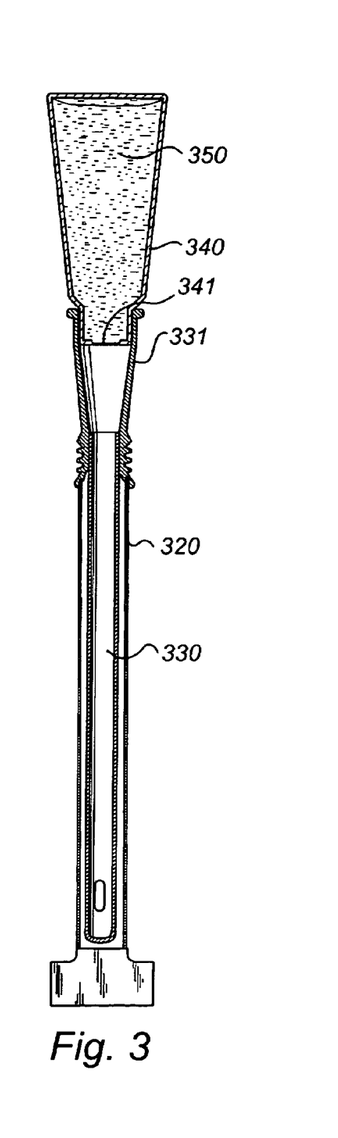
FIG. 3 is a partly broken side view of a third embodiment of a catheter assembly according to the invention, also presenting a separately enclosed wetting fluid, said embodiment in structure resembling another catheter assembly disclosed in WO 01/43807.

With reference to FIG. 3, a third embodiment of the catheter assembly will now be described. In this embodiment, the catheter assembly generally corresponds to the second embodiment in FIG. 2, the structure resembling catheter assemblies disclosed in WO 01/43807. In this case, however, the wetting fluid container 340 holding the wetting fluid 350 is formed as a separate compartment being separated from, and arranged outside the receptacle. However, in accordance with the inventive concept, the wetting fluid 350 and the fluid container 340 still forms part of the overall catheter assembly as such, i.e. are "assembled" with the other components. The fluid container 340 is arranged on and is maintained by the catheter connector 331, and a fluid connection between the fluid container and the catheter compartment is prevented by a rupturable separation wall 341.

For activation of the catheter, the user applies e.g. a compressing force to the separate wetting container 340 in such a way that the rupturable separation wall 341 is opened and wetting fluid is introduced into the catheter compartment via the connector and through the catheter lumen. Preferably, the wetting container contains a sufficient amount of wetting fluid for the insertable length of the catheter to be sufficiently wetted.

Figure 4A:
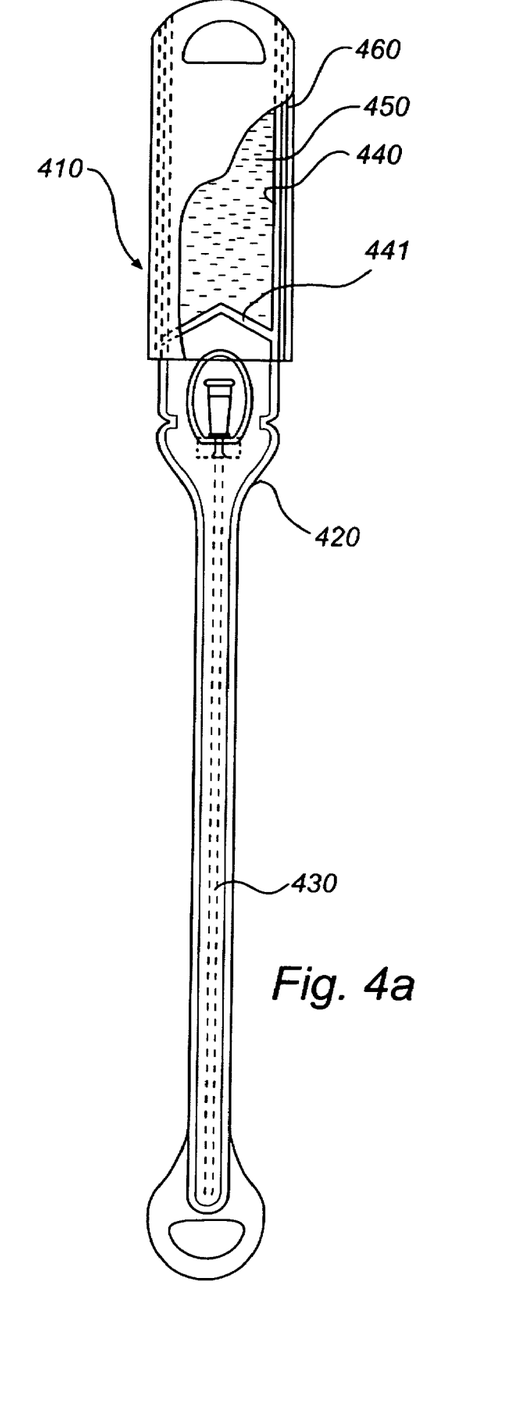
FIGS. 4a and 4b illustrate a fourth embodiment of a catheter assembly according to the invention. also presenting a separately enclosed wetting fluid, said embodiment in structure resembling another catheter assembly disclosed in WO 01/43807, FIG. 4a being a side view of the catheter assembly in a non-activated state of operation, and FIG. 4b being a side view of the catheter assembly during an activation process.
Figure 4B:
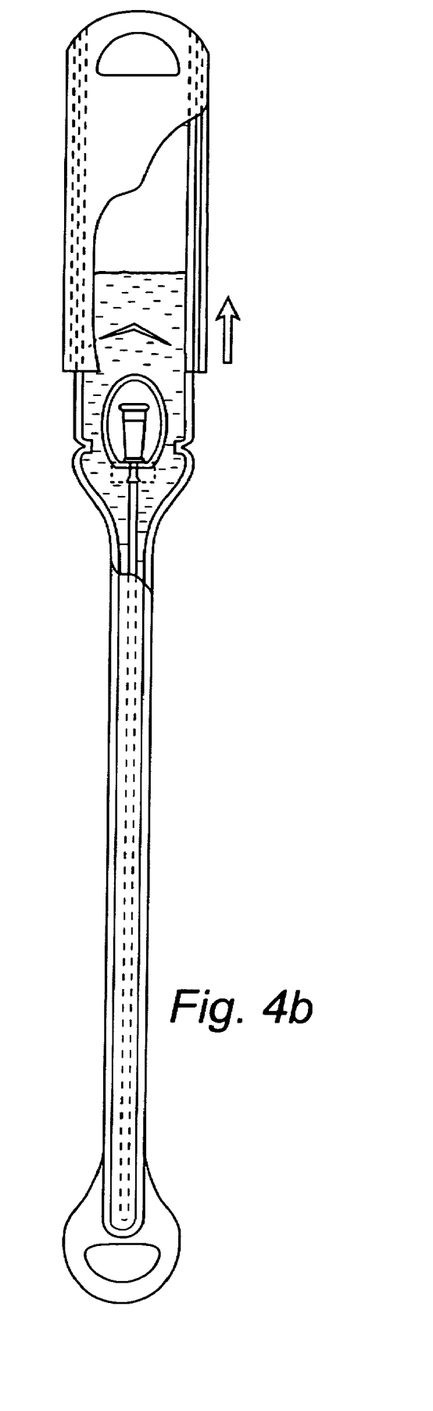

With reference to FIGS. 4a and 4b, a fourth embodiment of the catheter assembly will now be described. Also in this embodiment, the catheter assembly in structure resembles catheter assemblies disclosed in WO 01/43807. The catheter assembly 410 comprises a wetting receptacle or bag 420. As in the previously discussed embodiments, the catheter assembly comprises a hydrophilic catheter, and preferably a urinary catheter 430. The wetting receptacle encloses at least the insertable length of the catheter 430, but leaves at least part of the catheter 430 outside the wetting receptacle 420, said part comprising the connection interface. The assembly also comprises a wetting fluid container 440 containing a wetting fluid 450. In this embodiment, the wetting fluid container 440 is formed in a compartment of the wetting receptacle being separated from the compartment accommodating the catheter 430. The wetting fluid container 440 is arranged in a part of the receptacle extending rearward from the catheter 430, i.e. rearward of the connector part thereof. Said rearward part of the wetting receptacle 420 is preferably in fluid communication with the forward part housing the catheter 430. The wetting fluid compartment 440 is separated from the compartment holding the catheter 430 by means of a rupturable separation wall 441.

The wetting fluid 450 may be discharged into the other compartment of the receptacle by compressing the wetting fluid container 440, and/or by applying a pulling force between the end parts of the assembly.

In order to achieve a stronger and preferably gas impermeable wetting fluid compartment, it is preferred to arrange an additional cover 460 around said compartment 440. This additional cover 460 may be arranged on the inside of the wetting fluid compartment 440 formed in the receptacle 420, but is preferably arranged as an outer cover 460 arranged over the part of the receptacle 420 forming the wetting fluid compartment 440, as illustrated in FIG. 4.

For activation of the catheter 430 in FIG. 4, the user applies e.g. a compressing force to the wetting fluid compartment 440, thereby forcing open the separation joint 441 and discharging the wetting fluid into the catheter compartment, as is illustrated in FIG. 4b. Preferably, the wetting fluid container 440 contains a sufficient amount of wetting fluid 450 for the insertable length of the catheter to be sufficiently wetted. After release of the wetting fluid into the catheter compartment, the wetting receptacle 120 may be opened, e.g. at the distal end thereof, as is discussed above, for insertion of the catheter.

Figure 5:
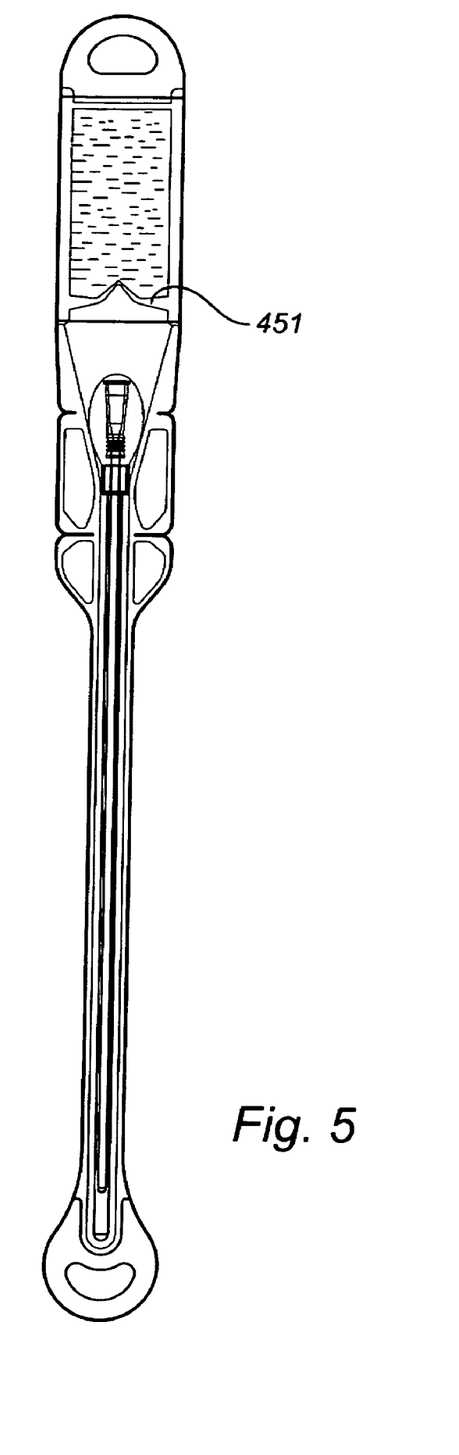
FIG. 5 is a partly broken side view of a fifth embodiment of a catheter assembly according to the invention, also presenting a separately enclosed wetting fluid, said embodiment in structure resembling another catheter assembly disclosed in WO 01/43807.

With reference to FIG. 5, a fifth embodiment of the catheter assembly will now be described. This embodiment resembles to a large extent the embodiment discussed with reference to FIG. 4, and also resembles the structure of some embodiments discussed in WO 01/43807. The most important differences between the embodiments in FIG. 4 and FIG. 5 are that the entire catheter is enclosed in the receptacle in the embodiment in FIG. 5, and that the wetting fluid compartment is configured somewhat differently.

More specifically, in the embodiment illustrated in FIG. 5, two sheets of outer cover material is arranged over the part of the wetting receptacle forming the wetting fluid container. Preferably, the outer cover material sheets are dimensioned essentially only to cover the wetting fluid container part of the receptacle.

Further, the separation between the wetting fluid compartment and the cavity accommodating the catheter provides a rupturable sealed closure 451, in which it is provided at least one point of weakness, in order for an induced rupture to occur in a predetermined position, thereby enabling fluid communication between the wetting fluid compartment and the compartment housing the catheter. In this embodiment this is achieved by means of a non-linear geometrical arrangement of the joint together with a weld width variation. The joint is here arranged with a knee directed towards the wetting fluid compartment. The knee has an angled peak portion directed towards the wetting fluid compartment. Further, this effect is supported and increased by an advantageously arranged width variation of the weld. Accordingly, the two parameters, weld width and geometrical arrangement, cooperates to form a very predictable and easily ruptured separation wall.

The method of activation of the catheter according to this embodiment resembles the wetting process discussed with reference to FIG. 4. After release of the wetting fluid into the catheter compartment, the wetting receptacle may be opened, e.g. at the distal end thereof, as is discussed above, for insertion of the catheter.

Figure 6:
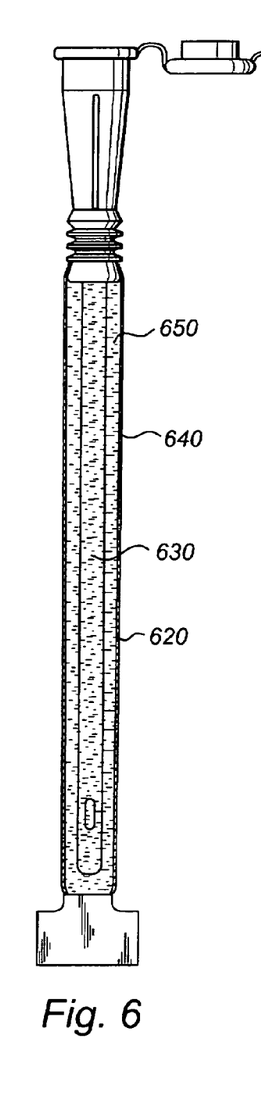
FIG. 6 is a partly broken side view of a sixth embodiment of a catheter assembly according to the invention, presenting a wetting fluid arranged in wetting contact with the hydrophilic surface layer, said embodiment in structure resembling a catheter assembly disclosed in WO 01/43807.

With reference to FIG. 6, a sixth embodiment of an catheter assembly will now be described. In this embodiment, the catheter assembly generally corresponds to the previously disclosed embodiments, and in particular to the second and third embodiments. Further, this embodiment in structure resembles catheter assemblies disclosed in WO 01/43807. In this embodiment, the wetting fluid container 640 is not formed in a separate compartment of the receptacle, but is integrated with the compartment holding the catheter. Hereby, the catheter is activated already during production, and is then maintained in a activated, ready-to-use condition. Thus, in this embodiment, the hydrophilic surface layer is preserved in a wetted state during accommodation in the receptacle and a ready-to-use catheter assembly is provided. In order to preserve this wetted condition the compartment formed by the receptacle and the catheter is preferably gas sealed, and further, the receptacle is preferably gas impermeable.

In use, the receptacle is simply opened, and the catheter could immediately be introduced into the patient.

Figure 7:
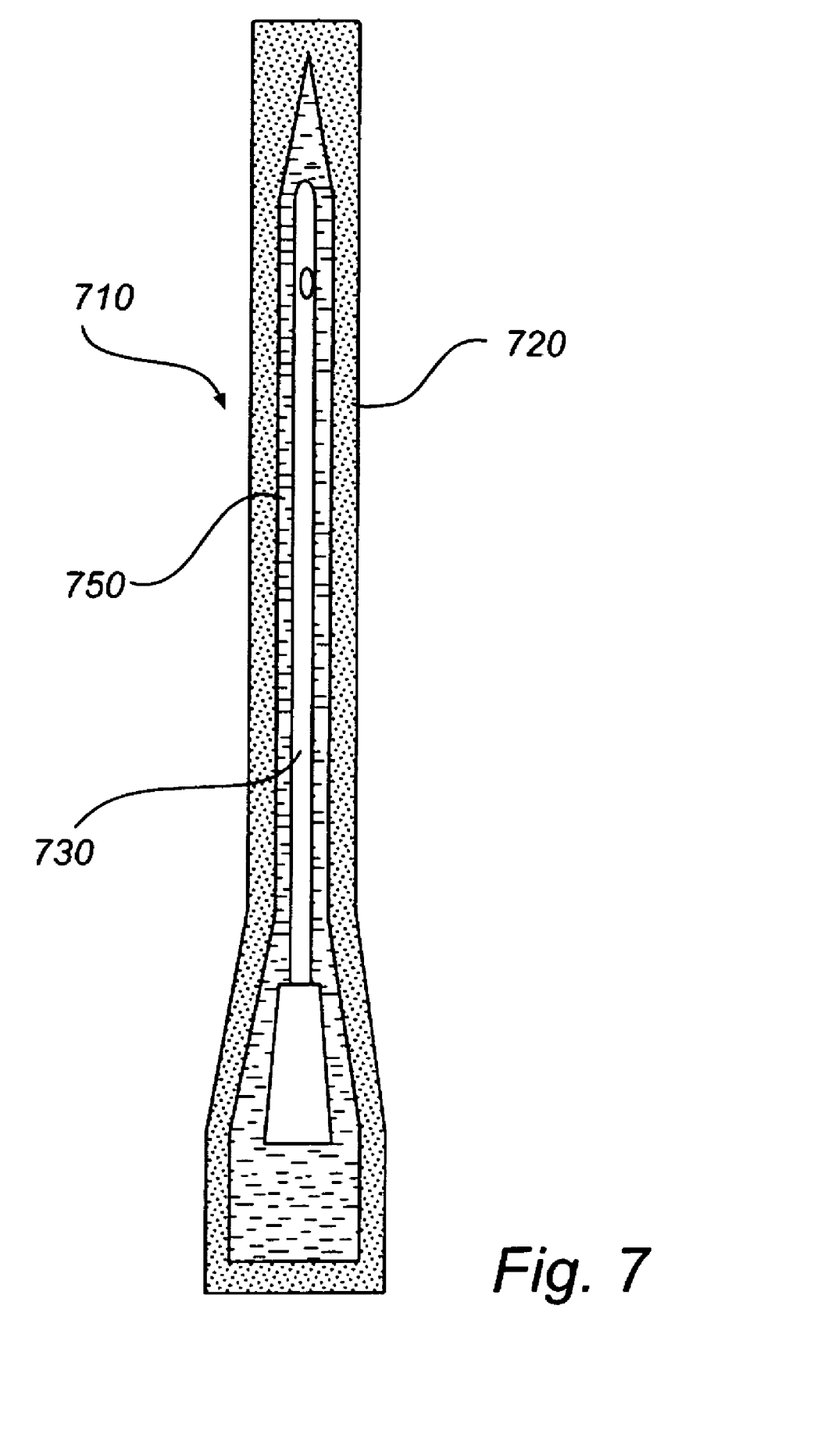
FIG. 7 is a partly broken side view of a seventh embodiment of a catheter assembly according to the invention, presenting a wetting fluid arranged in wetting contact with the hydrophilic surface layer, said embodiment in structure resembling a catheter assembly disclosed in WO 00/47494.

With reference to FIG. 7, a seventh embodiment of the catheter assembly will now be described, the structure of which generally resembles embodiments disclosed in WO 00/47494, hereby incorporated by reference.

Like in the embodiment in FIG. 6, this embodiment relates to a catheter assembly 710 in which the wetting receptacle 720 encloses the wetting fluid 750 and the catheter 730 in such a way that the wetting fluid is in direct wetting contact with the hydrophilic surface of the catheter during storage, i.e. the catheter is continuously kept in an activated state. However, in this embodiment the receptacle is formed to enclose the entire catheter.

Measuring Method Using Artificial Urethra

Previously known friction measurement methods for catheters do not take into consideration the special circumstances and conditions prevailing in the urethra. Accordingly, said methods fail to provide reliable information on the extraction force actually needed for removal of catheters in the use situation and, consequently, also fail to provide information on the possible pain and suffer the patient may endure.

Accordingly, there is a need for an improved method for measuring the extraction force from the urethra for urinary catheters, taking into account at least some parameters specific for the environment of the intended use, such as the constituents of the surrounding fluids (in the epithelial cells), the circumferential enclosing of the catheter shaft and the pressure thereby applied to the catheter, the frictional properties of the inner urethra wall (epithelium), the dehydration of the hydrophilic surface occurring within the urethra, etc.

To this end, an improved measuring method involving an artificial urethra, as discussed in more detail in the following, is hereby proposed by the present inventors.

The newly developed measuring method has been developed for measuring extraction friction during removal of a catheter from the urethra, where several parameters are taken into account, such as:

the pressure in the urethra, which is normally between 2.4-13.7 kPa.

the concentration relations.

the catheterization time period.

The measurement results reflect how firmly the catheter is held in the urethra, i.e. how sticky the catheter surface is to the inner urethra wall (epithelium).

In the measuring method, the mucous membrane of the urethra is simulated with an artificial urethra, accomplished by means of a dialysis membrane formed as a tube. For the measurement, the catheter is placed in the membrane, and the entire assembly is placed in a saline solution with the same concentration of osmolality increasing compound as in ordinary urine, and maintained in said solution during a time period corresponding to the catheterization time period. Subsequently, a pressure is applied to the catheter by means of the artificial urethra to form a constant pressure, said pressure being established with applied air pressure. The force required for the withdrawal of the catheter is measured by means of a dynamometer or the like. The measured force is a measure on the extraction force required to withdraw the catheter from a urethra in the actual use situation, and is therefore also a measure on the friction between the urethra and the catheter surface.

It has been found that the results of said measuring method provide a very good conformity with other measurements performed on urethras in vitro, as well as with in vivo measurements.

The measuring device simulating the urethra comprises a dialysis membrane formed as a tube, into which the catheter may be introduced. The pore size of the dialysis membrane is preferably chosen to be approximately MWCO (Molecular Weight Cut Off) 500 Dalton. For example, the dialysis membrane Spectra/Por® CE (Cellulose Ester) membrane MWCO 500 may be used. The membrane provides a gel-like surface when wetted, which provides a good resemblance with the mucous membrane of the urethra.

Pressure applying means are arranged around the inner tube made of dialysis membrane. These pressure applying means may comprise an outer tube of a relatively rigid material arranged coaxially outside the inner tube, and an inflatable bag arranged between the inner and outer tubes. The inflatable bag could be made of a plastic film, e.g. EBA foil (polyethylene butyl acrylate). Pressure regulating means, such as a pump, and pressure sensing means are connectable to the inflatable bag for controlling the pressure applied to the catheter through the dialysis membrane.

For the measurement, the catheter is wetted as in ordinary use, and thereafter placed in the membrane.

The entire assembly is then placed in a saline solution with a salt concentration resembling the one in ordinary urine. The solution preferably comprises NaCl, and the concentration is preferably about 3.0% of weight. However, even other values could be used, such as 4% of weight NaCl, or 0% of weight NaCl, i.e. distilled water, in order to simulate extreme situations.

The assembly is maintained in said solution during a time period corresponding to the catheterization time period to be measured, which is normally in the range 0.5-10 minutes, and preferably about 5 minutes. For measurements of short time periods, the dialysis membrane may even be pre-wetted with the saline solution before the introduction of the catheter.

Subsequently, a pressure is applied to the catheter by means of the artificial urethra to form a constant pressure, said pressure e.g. being established with applied air pressure, as discussed above.

With the measuring device as discussed above, the pressure is controllable within a wide range. However, the pressure is preferably set to a value of about 10 kPa in the measurements, since this is pressure corresponding to the pressure experienced in an ordinary urethra in a living person. The pressure may also be set slightly above this range, preferably at about 14 kPa, in order to obtain a maximum friction and force measurement value that is not exceeded during ordinary use.

The withdrawal of the catheter is made with a dynamometer, e.g. Mecmesin Force Gauge, for measuring the extraction force required. Preferably, the retraction is made with a constant speed, which could be achieved by using a so called pull testing device, e.g. Mecmesin VersaTest.

The relation between the extraction force and the pressure is generally:

$$F = \mu * P * A \quad (1)$$

where, F is the required extraction force [N], $\mu$ is the coefficient of friction, P is the applied pressure [Pa] and A is the area [m$^2$].

EXPERIMENTS

In an experimental tests, the method using an artificial urethra was used. Two different types of catheters were used: LoFric®, which is commercially available from AstraTech AB, and Speedicath®, which is commercially available from Coloplast AS.

Each of the catheters were wetted with a wetting solution comprising an osmolality-increasing compound (predominantly NaCl) of about 500, 700 and 900 mOsm/dm$^3$, respectively, and the wetting period was about 1 minute before testing. The experimental set-up for the testing was the same for all the catheters, and a saline solution surrounding the artificial urethra had a salt concentration resembling the one in ordinary urine, viz. about 3.0% of weight. The measured extraction force required for the different catheters are illustrated in table 1 below:

TABLE 1

Measurement of extraction force from an artificial urethra for catheters wetted in different wetting fluid solutions

| Catheter type, and concentration of the osmolaltiy increasing compound in the wetting fluid | Extraction force (N) | Standard deviation |
|---|---|---|
| LoFric ®, about 500 mOsm/dm$^3$ | 1.8 | 0.41 |
| LoFric ®, about 700 mOsm/dm$^3$ | 0.9 | 0.21 |
| LoFric ®, about 900 mOsm/dm$^3$ | 0.9 | 0.19 |
| Speedicath ®, about 500 mOsm/dm$^3$ | 3.3 | 1.20 |
| Speedicath ®, about 700 mOsm/dm$^3$ | 2.1 | 0.80 |
| Speedicath ®, about 900 mOsm/dm$^3$ | 2.0 | 0.84 |

As is clearly evident from the measurements illustrated in table 1, there is a dramatic improvement and decrease in the required extraction force when wetting fluids having an osmolality level of 700 mOsm/dm$^3$ or above is used, compared to when a level of 500 mOsm/dm$^3$ is used. This effect is clearly visible in both the catheter types discussed above, and on which the experimental testing were conducted.

In another line of experiments, the difference in stability during wetting was studied between catheters in which the osmolality increasing compound was integrated in the hydrophilic coating as compared to where the osmolality increasing compound was dissolved in the wetting fluid.

In this experimental tests, the LoFric® catheter, as discussed above, was used. Two different preparations of these catheters were used:

1. Catheters with hydrophilic coatings comprising PVP K90, and in which an osmolality increasing compound (here NaCl) is incorporated into the hydrophilic coating in the way disclosed in e.g. EP 0 217 771. These catheters were wetted in distilled water, i.e. in a wetting fluid without any dissolved osmolality increasing compound.
2. The same type of catheters as in 1), with hydrophilic coatings comprising PVP K90, but without any osmolality increasing compound. These catheters were wetted with a wetting fluid comprising a dissolved osmolality increasing compound. The wetting fluid comprised 3.0% weight of NaCl.

The catheters were wetted in the wetting fluid as specified above during 5 seconds, 30 seconds or 5 minutes. It is to be noted that a recommended wetting duration for this type of catheters is normally about 30 seconds, but intentional and unintentional variations may occur in actual use. The osmolality of the wetted surface was determined by means of a conductivity test (the conductivity, e.g. measured as µS/cm, is proportional to the salt concentration, e.g. measured as mg(NaCl)/area unit). The results are presented in table 2.

TABLE 2

Measurement of osmolality on the wetted catheter surface in dependence on different wetting times

| Wetting time | Catheter 1 | Catheter 2 |
|---|---|---|
| 5 s | 1508 mOsm/dm$^3$ | 802 mOsm/dm$^3$ |
| 30 s | 558 mOsm/dm$^3$ | 828 mOsm/dm$^3$ |
| 5 min | 192 mOsm/dm$^3$ | 891 mOsm/dm$^3$ |

As is clearly evident from the measurements illustrated in table 2, there is a dramatic improvement in stability in the catheter 2) in which the osmolality increasing compound is dissolved in the wetting fluid, compared to catheter 1) in which the osmolality increasing compound is incorporated in the hydrophilic coating.

In still another line of experiments, the difference in water retention in ambient air was studied between catheters in which the osmolality increasing compound was integrated in the hydrophilic coating as compared to where the osmolality increasing compound was dissolved in the wetting fluid. The same two types of catheters as in the experiment discussed in relation to table 2 were used.

Again, the catheters were wetted in the wetting fluid as specified above during 5 seconds, 30 seconds or 5 minutes. The were allowed to dry in ambient air for a period of 1 minute or 6 minutes, and where then weighed. The weight was compared to the weight of the un-wetted catheter, and the difference was calculated, and serves as a measure of the amount of wetting fluid held by the hydrophilic coating, It is to be noted that the water retention in ambient air is an important parameter since in practical use, a time period may elapse between the wetting of the catheter and the subsequent insertion into the urethra. However, the water retention in ambient air and the water retention in the urethra are not necessarily the same, or even necessarily correlated. The results of the measurements are presented in table 3.

TABLE 3

Measurement of water retention in the wetted catheter surface in dependence on different wetting times and after allowing to dry in ambient air for a period of 1 minute or 6 minutes, respectively.

| Wetting time | Catheter 1 | | Catheter 2 | |
| --- | --- | --- | --- | --- |
| | 1 minute | 6 minutes | 1 minute | 6 minutes |
| 5 s | 7.90 mg/cm$^2$ | 5.03 mg/cm$^2$ | 8.43 mg/cm$^2$ | 5.93 mg/cm$^2$ |
| 30 s | 9.31 mg/cm$^2$ | 5.85 mg/cm$^2$ | 11.69 mg/cm$^2$ | 8.58 mg/cm$^2$ |
| 5 min | 10.24 mg/cm$^2$ | 6.46 mg/cm$^2$ | 14.22 mg/cm$^2$ | 9.68 mg/cm$^2$ |

As is clearly evident from the measurements illustrated in table 2, the wetting fluid content in the catheters 2 are significantly higher than in the catheters 1, and the water retention in the catheters wetted by a wetting fluid in which the osmolality increasing compound is dissolved is apparently improved over the water retention in the catheters having a corresponding concentration of osmolality increasing compound in the coating.

Conclusion and Summary

In the foregoing, a catheter assembly has been disclosed comprising: a hydrophilic catheter; a wetting fluid for wetting of the catheter; and a receptacle enclosing at least the insertable part of the catheter. Further, the wetting fluid comprises at least one dissolved osmolality-increasing compound, wherein the total concentration of the dissolved osmolality-increasing compound(s) is very high, exceeding 600 mOsm/dm$^3$. The wetting fluid could either be arranged in contact with the hydrophilic surface layer of the catheter in the receptacle, for preservation of the hydrophilic surface layer in a wetted state during accommodation in said receptacle and provision of a ready-to-use catheter assembly, or be arranged to keep the wetting fluid separated from the hydrophilic surface layer of the catheter during storage, but to be brought into contact with said hydrophilic surface layer upon activation before an intended use of the catheter. A similar method, use, catheter and wetting fluid are disclosed as well.

The provision of at least one osmolality-increasing compound in the wetting fluid provides several advantages per se, such as a improved properties of the hydrophilic coating, a more predictable and controllable wetting process, a more expedient and cost efficient production, etc. Further, the use of the inventive very high concentration of osmolality-increasing compound(s) in the wetting fluid has proven remarkably efficient.

The invention has now been discussed in relation to different embodiments. However, it should be appreciated by those versed in the art that several further alternatives are possible. For example, the features of the different embodiments discussed above may naturally be combined in many other ways.

It is further possible to use the invention for other types of catheters than urinary catheters, such as vascular catheters or the like. It is also possible to use many different types of osmolality-increasing compounds in the wetting fluid, either alone or in different combinations. Many different levels of concentration of the osmolality-increasing compounds above 600 mOsm/dm$^3$ are also feasible, even though the higher levels proposed in the foregoing are normally more advantageous.

Still further, it is possible to arrange the wetting fluid container in many different ways. For example, the container may be a separate container, but forming part of the assembly. Such a wetting fluid container may be arranged completely inside the receptacle, partly inside the receptacle, or completely outside the receptacle. Alternatively, the wetting fluid container may be an integrated compartment of the receptacle. This compartment may be separated from the compartment housing the insertable part of the catheter, or be integrated with such a compartment. In the latter case, the catheter may be maintained in a wetted, activated state.

Further, the wetting fluid container may be arranged close to the distal part of the catheter, close to the proximal part of the catheter, or in any other suitable location in the assembly. In case the wetting fluid is arranged separately from the insertable part of the catheter, the separation wall or joint could e.g. be a breakable or peelable membrane wall, but alternative embodiments are naturally feasible, such as various types of detachable or openable caps or closings. The wetting fluid container may be arranged to be discharged upon application of a twist, a compression, a pull or the like on the fluid container. Preferably the wetting fluid may be discharged without breaking or rupturing the receptacle, even though this may not be necessary, depending on the intended use, etc.

Many different materials could also be used for the different parts of the catheter assembly.

It will be appreciated by those versed in the art that several such alternatives similar to those described above could be used without departing from the spirit of the invention, and all such modifications should be regarded as a part of the present invention, as defined in the appended claims.

The invention claimed is:

1. A catheter assembly comprising:
   a wetting fluid; and
   a catheter having on its surface, on at least an insertable part thereof, a hydrophilic surface layer providing low-friction surface character of the catheter by treatment with said wetting fluid; and a receptacle enclosing at least the insertable part of the catheter,
   wherein the assembly presents a storage state in which the wetting fluid is kept separated from the hydrophyllic surface layer of the catheter, and an activation state in which the wetting fluid is brought into contact with said hydrophyllic surface layer before an intended use of the catheter, and
   wherein the wetting fluid, in the storage state, comprises at least one dissolved osmolality-increasing compound, wherein the total concentration of the dissolved osmolality-increasing compound(s) exceeds 600 mOsm/dm$^3$.

2. The catheter assembly as claimed in claim 1, wherein the total concentration of the osmolality-increasing compound(s) in the wetting fluid exceeds 700 mOsm/dm$^3$.

3. The catheter assembly as claimed in claim 1, wherein the total concentration of the osmolality-increasing compound(s) in the wetting fluid is in the range of 850 to 950 mOsm/dm$^3$.

4. The catheter assembly as claimed in claim 1, wherein the total concentration of the osmolality-increasing compound(s) in the wetting fluid is greater than 600 mOsm/dm$^3$s and less than 1500 mOsm/dm$^3$.

5. The catheter assembly as claimed in claim 1, wherein said osmolality-increasing compound(s) is/are selected from the group consisting of urea, amino acids, mono and disaccharides, sugar alcohols, and non-toxic organic and inorganic salts or acids, polypeptides and mixtures thereof.

6. The catheter assembly as claimed in claim 5, wherein said osmolality-increasing compound(s) is/are selected from the group consisting of glucose, sorbitol, sodium chloride, sodium citrate, sodium benzoate, calcium chloride, potassium chloride, potassium iodide and potassium nitrate.

7. The catheter assembly as claimed in claim 1, wherein the said wetting fluid further comprises a polymer.

8. The catheter assembly as claimed in claim 7, wherein the polymer is a hydrophilic polymer.

9. The catheter assembly as claimed in claim 7, wherein the amount of polymer in the wetting fluid is in the range 0-20% of weight.

10. The catheter assembly as claimed in claim 1, wherein the wetting fluid is a water-based liquid.

11. The catheter assembly as claimed in claim 1, wherein the catheter is a urinary catheter is adapted for intermittent use.

12. The catheter assembly as claimed in claim 1, wherein said wetting receptacle encloses the entire catheter.

13. The catheter assembly as claimed in claim 1, wherein said receptacle entirely encloses said wetting fluid.

14. The catheter assembly as claimed in claim 1, further comprising a separate wetting fluid container, which encloses said wetting fluid and which forms part of said catheter assembly.

15. A method for producing a catheter assembly, comprising:
    providing a receptacle;
    providing a hydrophilic catheter;
    providing a wetting fluid;
    arranging at least an insertable part of the catheter in the receptacle and arranging said wetting fluid as a part of said catheter assembly;
    wherein the assembly presents a storage state in which the wetting fluid is kept separated from the hydrophyllic surface layer of the catheter, and an activation state in which the wetting fluid is brought into contact with said hydrophyllic surface layer before an intended use of the catheter,
    said wetting fluid comprising at least one dissolved osmolality-increasing compound, the total concentration of the osmolality-increasing compound(s) exceeding 600 mOsm/dm$^3$.

16. The method as claimed in claim 15, wherein the total concentration of the osmolality-increasing compound(s) in the wetting fluid exceeds 700 mOsm/dm$^3$.

17. The method as claimed in claim 15, wherein the total concentration of the osmolality-increasing compound(s) in the wetting fluid is in the range of 850 to 950 mOsm/dm$^3$.

18. The method as claimed in claim 15, wherein the total concentration of the osmolality-increasing compound(s) in the wetting fluid is greater than 600 mOsm/dm$^3$ and less than 1500 mOsm/dm$^3$.

19. The method of claim 15, wherein the osmolality-increasing compound is selected from the group consisting of urea, amino acids, mono and disaccharides, sugar alcohols, and non-toxic organic and inorganic salts or acids, polypeptides and mixtures thereof.

20. The method of claim 15, wherein the wetting fluid is a water-based liquid.

21. The catheter assembly as claimed in claim 2, wherein the total concentration of the osmolality-increasing compound(s) in the wetting fluid exceeds 800 mOsm/dm$^3$.

22. The catheter assembly as claimed in claim 3, wherein the total concentration of the osmolality-increasing compound(s) in the wetting fluid is 900 mOsm/dm$^3$.

23. The method as claimed in claim 16, wherein the total concentration of the osmolality-increasing compound(s) in the wetting fluid exceeds 800 mOsm/dm$^3$.

24. The method as claimed in claim 17, wherein the total concentration of the osmolality-increasing compound(s) in the wetting fluid is about 900 mOsm/dm$^3$.

25. The catheter assembly as claimed in claim 8, wherein the polymer is the same type of hydrophilic polymer as in the hydrophilic surface layer of the catheter.

26. The catheter assembly as claimed in claim 9, wherein the amount of polymer in the wetting fluid is in the range 5-15% by weight.

27. The catheter assembly as claimed in claim 9, wherein the amount of polymer in the wetting fluid is about 10%.

28. A pre-packaged intermittent use type catheter assembly, comprising:
    a wetting fluid having a dissolved compound; and
    a catheter having on an insertable part of its surface, a hydrophilic surface layer adapted to provide a low-friction surface characteristic when contacted by the wetting fluid; and
    a receptacle enclosing at least a part of the catheter adapted to be inserted into the bladder of a user,
    wherein the assembly has a container in the receptacle for storing the wetting fluid separately from the hydrophyllic surface layer of the catheter, and for releasing the wetting fluid into the receptacle to contact said hydrophyllic surface layer before removal of the catheter from the receptacle and insertion into the bladder of a patient,
    wherein the wetting fluid dissolved compound is an osmolality-increasing compound and the total concentration of the dissolved osmolality-increasing compound in the wetting fluid that is separately stored in the container exceeds 600 mOsm/dm$^3$, and
    wherein when the amount of water retention in a catheter surface wetted by the wetting solution for a period of about 5 minutes and dried in ambient air for a period of about six minutes is in a range of from about 6.46 milligrams/square centimeter to about 9.68 milligrams per square centimeter.

* * * * *